United States Patent
Thouément et al.

(10) Patent No.: US 10,149,696 B2
(45) Date of Patent: Dec. 11, 2018

(54) MEDICAL INSTRUMENT

(71) Applicant: Karl Storz SE & Co. KG, Tuttlingen (DE)

(72) Inventors: Yann Thouément, Les Essarts le Roi (FR); Régis Besse, Guyancourt (FR)

(73) Assignee: Karl Storz SE & Co. KG, Tuttlingen (DE)

( * ) Notice: Subject to any disclaimer, the term of this patent is extended or adjusted under 35 U.S.C. 154(b) by 101 days.

(21) Appl. No.: 15/296,830

(22) Filed: Oct. 18, 2016

(65) Prior Publication Data

US 2017/0105747 A1 Apr. 20, 2017

(30) Foreign Application Priority Data

Oct. 19, 2015 (DE) .......................... 10 2015 117 731

(51) Int. Cl.
*A61B 17/29* (2006.01)
*A61B 18/14* (2006.01)
(Continued)

(52) U.S. Cl.
CPC .......... *A61B 17/2909* (2013.01); *A61B 17/29* (2013.01); *A61B 18/1445* (2013.01);
(Continued)

(58) Field of Classification Search
CPC . A61B 17/2909; A61B 17/29; A61B 18/1445; A61B 17/28; A61B 2017/2938; A61B 17/2841

See application file for complete search history.

(56) References Cited

U.S. PATENT DOCUMENTS 5,472,439 A * 12/1995 Hurd ...................... A61B 17/29
606/1
8,133,244 B2 * 3/2012 Bacher ............. A61B 17/32002
606/1
(Continued)

FOREIGN PATENT DOCUMENTS

EP 2095778 A1 9/2009
EP 2581059 A1 4/2013
(Continued)

OTHER PUBLICATIONS

German Search Report Application No. 10 2015 117 731.5 Completed: Aug. 11, 2016; dated Aug. 15, 2016 7 Pages.
(Continued)

*Primary Examiner* — Katrina Stransky
(74) *Attorney, Agent, or Firm* — Whitmyer IP Group LLC

(57) ABSTRACT

A medical instrument having an elongated shaft, with an elongated outer tube, a first transmission element including a first and second half tube, mutually displaceable in a longitudinal direction in order to operate one first functional element, wherein a second transmission element is in a cavity formed by the first and second half tube. A shaft housing connected to the outer tube is arranged in a proximal end portion of the shaft, and a first hollow tube which is connected to the first half tube is arranged within the shaft housing, and a second hollow tube connected to the second half tube within the first hollow tube, with substantially annular first and second seals. The first and second half tube extend through the shaft housing, a seal is arranged between an inner surface of the shaft housing and the outer surfaces of the first and second half tube.

20 Claims, 9 Drawing Sheets

(51) Int. Cl.
*A61B 17/00* (2006.01)
*A61B 90/70* (2016.01)

(52) U.S. Cl.
CPC ......... *A61B 90/70* (2016.02); *A61B 2017/003* (2013.01); *A61B 2017/2912* (2013.01); *A61B 2017/2927* (2013.01); *A61B 2017/2948* (2013.01); *A61B 2217/007* (2013.01); *A61B 2218/002* (2013.01)

(56) References Cited

U.S. PATENT DOCUMENTS

| | | | | |
|---|---|---|---|---|
| 8,702,740 B2* | 4/2014 | Oberlaender | ...... | A61B 17/1611 606/184 |
| 9,011,484 B2* | 4/2015 | Reinauer | ............ | A61B 17/2909 606/205 |
| 9,539,061 B2* | 1/2017 | Imuta | .................... | A61B 34/71 |
| 9,579,089 B2* | 2/2017 | Kaercher | ................ | A61B 17/00 |
| 9,599,166 B2* | 3/2017 | Stefan | .................... | A61B 17/29 |
| 9,662,131 B2* | 5/2017 | Omori | .................... | A61B 17/29 |
| 9,936,966 B2* | 4/2018 | Castro | .................... | A61B 17/29 |
| 2004/0243125 A1* | 12/2004 | Dycus | ................. | A61B 18/1445 606/51 |
| 2015/0119918 A1* | 4/2015 | Blase | ................. | A61B 17/3421 606/170 |
| 2016/0022122 A1* | 1/2016 | Dejima | .............. | A61B 1/00087 600/210 |
| 2017/0164973 A1* | 6/2017 | Lesko | .............. | A61B 17/32009 |
| 2017/0164997 A1* | 6/2017 | Johnson | ............. | A61B 18/1445 |

FOREIGN PATENT DOCUMENTS

| | | |
|---|---|---|
| EP | 2837354 A1 | 2/2015 |
| WO | 2010105649 A1 | 9/2010 |

OTHER PUBLICATIONS

European Search Report Application No. 16 19 3872 Completed: Nov. 10, 2016; dated Nov. 18, 2016 6 pages.

* cited by examiner

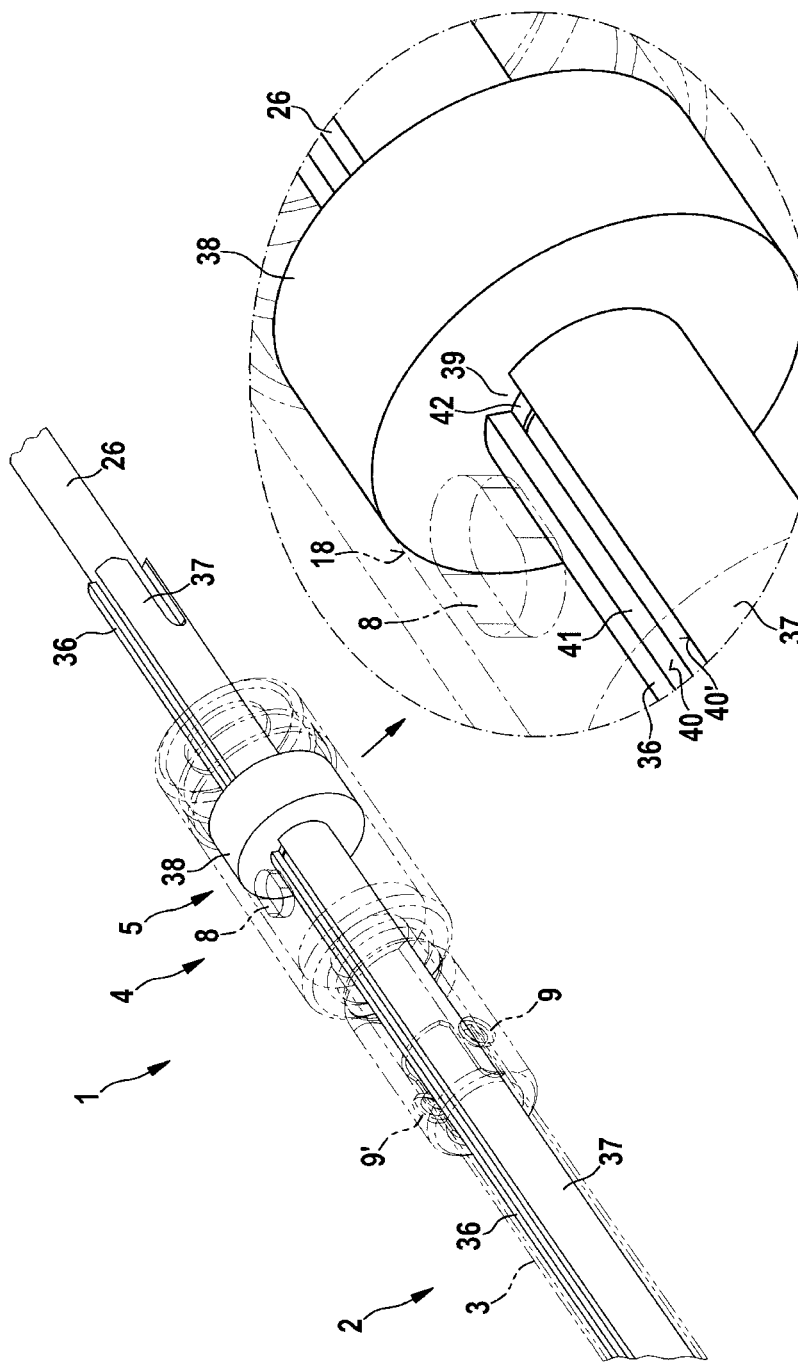

MEDICAL INSTRUMENT

TECHNICAL FIELD

The present invention relates to a medical instrument having an elongate shaft, a tool arrangement arranged at a distal end of the shaft and a handle, which is arranged at a proximal end of the shaft, for operating the tool arrangement.

BACKGROUND

Medical instruments of this type are known. In particular, European patent application EP 2 837 354 A1, which is incorporated by reference into the present application, discloses a medical manipulator having a shaft, a working portion, which is arranged at the tip thereof, with a gripper, and a handle with which the gripper can be operated. The working portion has a bending portion between the gripper and the shaft, said bending portion bringing about an angling of the gripper from an axial direction of the shaft on account of a bending operating force transmitted from the handle. Extending within an outer tube of the shaft are a first and a second half tube which are each designed as a hollow tube divided along its longitudinal axis and which, facing each other with their open sides, are arranged parallel to each other and which are displaceable in the longitudinal direction of the shaft. The first and the second half tube are connected to sliding elements guided on mutually opposite sides of the bending portion. By means of mutual displacement of the half tubes in the longitudinal direction of the shaft, bending of the bending portion can be brought about via a corresponding displacement of the sliding elements. Extending within the two half tubes is an inner tube, the rotation of which about the longitudinal axis of the shaft can cause the gripper to rotate about a longitudinal axis of the gripper, and the displacement of which in the longitudinal direction of the shaft can cause the gripper to open or close. The inner tube extends into the bending portion and follows a bending of the bending portion. Electric lines extend within the inner tube and by means of which the gripping elements of the gripper are connected to a high frequency voltage source. The handle comprises a hand grip with which a user can hold the medical manipulator, and also control elements for controlling the mentioned functions of the working portion.

In the case of medical instruments, in particular in the case of reusable medical instruments, at least those parts of the instrument that may come into contact with body fluids have to be able to be cleaned and/or sterilized. In the case of endoscopic medical instruments, this applies at least to those parts of the instrument which are intended for introduction into a cavity inside a human or animal body. Cleaning with a cleaning fluid or sterilization with a liquid or gaseous sterilization fluid, for example, are possible for this purpose.

SUMMARY

It is an object of the present invention to specify a medical instrument of the type in question which is improved in respect of its cleaning and/or sterilization possibilities.

This object is achieved by a medical instrument according to the different features of the present invention.

Advantageous developments of the invention emerge from the dependent claims.

A medical instrument according to the invention has an elongate shaft of preferably rigid design. The medical instrument is designed in particular as an endoscopic instrument, wherein the shaft is designed at least in sections for introduction into a cavity inside a human or animal body. The medical instrument can be, for example, a manipulator with which, in the event of an endoscopic procedure, surgical manipulations can be undertaken in the cavity inside the body.

Furthermore, the medical instrument comprises a tool arrangement which is arranged at the distal end of the shaft, i.e. the end remote from the user, and which is designed in particular for carrying out surgical manipulations in the cavity inside the body. Furthermore, the medical instrument comprises a handle which is arranged at a proximal end of the shaft, i.e. at the end close to the user, and which serves for operation of the tool arrangement by means of a user and which, for this purpose, can have one or more control elements and also a hand grip.

The shaft of the medical instrument according to the invention has an elongate outer tube which is of substantially hollow-cylindrical design and the length and outer diameter of which are selected in particular in such a manner that said outer tube can be introduced at least with a distal portion into the cavity inside the human or animal body. The distal portion of the shaft and the tool arrangement can therefore be introduced into the cavity inside the body. A first transmission element which is designed for transmitting an operating movement from the handle to the tool arrangement in order to operate at least one first functional element of the tool arrangement is arranged within the outer tube, i.e. in the elongate cavity formed by the substantially hollow-cylindrical outer tube. The first functional element comprises in particular at least one movable component which can be moved by means of the first transmission element. For this purpose, the first transmission element is directly or indirectly connected on the distal side to the at least one first functional element of the tool arrangement and on the proximal side to a corresponding operating device of the handle. The first transmission element can likewise be of substantially hollow-cylindrical design.

The first transmission element comprises a first and a second half tube which each have a curved, preferably an approximately semicircular cross section. The first and the second half tube constitute in particular the two parts of a cylindrical hollow tube which is sectioned in its longitudinal direction along a longitudinal center plane. The first and the second half tube are arranged facing each other with their respective longitudinal-side openings, and therefore overall they approximately form a hollow cylinder. The longitudinal sectional surfaces of the first and the second half tube are opposite each other here and can in each case form a gap in between. The hollow cylinder formed by the first and the second half tube is preferably arranged coaxially within the outer tube of the shaft, and therefore the center longitudinal axis of the hollow cylinder formed by the first and the second half tube approximately coincides with the center longitudinal axis of the outer tube. In particular, the first and the second half tube can each take up, as seen from the center longitudinal axis, an arc of approximately 180°, or of somewhat less than 180° in the case in which a gap is provided between the first and the second half tube. The first and the second half tube are mounted so as to be displaceable relative to the outer tube and are displaceable relative to each other in order to operate the first functional element of the tool arrangement.

Furthermore, a second transmission element which is designed for transmitting an operating movement from the handle to the tool arrangement in order to operate at least one second functional element of the tool arrangement is arranged within the first transmission element, i.e. in an elongate cavity formed by the first half tube and the second half tube. The second functional element comprises in particular at least one movable component which can be moved by means of the second transmission element. For this purpose, the second transmission element is directly or indirectly connected on the distal side to the second functional element and on the proximal side to a corresponding operating device of the handle.

According to the invention, a shaft housing which is enlarged in relation to the outer tube and is connected fluid-tightly to the outer tube, in particular to a proximal end of the outer tube, is provided in a proximal end portion of the shaft. The shaft of the medical instrument according to the invention therefore comprises at least one distal portion in which the outer tube forms a radial outer surface of the shaft and which is suitable in particular for introduction into a cavity inside a body, and a proximal end portion, the radial outer surface of which is enlarged in relation to the at least one distal portion and is formed, for example, cylindrically with a larger outer diameter than said distal portion. The shaft housing is arranged in particular between the distal portion of the shaft and the handle. The outer tube can extend in sections into the shaft housing. Furthermore, a first hollow tube which is of substantially cylindrical design, is closed circumferentially and is connected to the first half tube, in particular to a proximal end of the first half tube, is arranged at least in sections within the shaft housing. A second hollow tube which is likewise of substantially cylindrical design and is closed circumferentially and is connected to the second half tube, in particular to a proximal end of the second half tube, is arranged at least in sections within the first hollow tube. The first hollow tube is displaceable together with the first half tube, and the second hollow tube together with the second half tube, in the longitudinal direction relative to the shaft housing.

Furthermore, according to the invention, a first seal of substantially annular design is arranged between a preferably cylindrical inner surface of the shaft housing and a preferably cylindrical outer surface of the first hollow tube, and a second, likewise substantially annular seal is arranged between an inner surface of the first hollow tube and an outer surface of the second hollow tube.

Owing to the fact that the first half tube is connected on the proximal side to a first hollow tube and that the second half tube is connected on the proximal side to a second hollow tube, which is arranged at least in sections within the first hollow tube, and also that a respective substantially annular seal is arranged between the shaft housing, which is connected to the outer tube, and the first hollow tube, and between the first and the second hollow tube, it is made possible to introduce a cleaning liquid or a sterilization fluid into a cavity formed between the outer tube and the first and the second half tube without said cleaning liquid or sterilization fluid being able to escape from the shaft on the proximal side. This creates the possibility of irrigating the arrangement formed by the outer tube and the first and the second transmission element with a cleaning liquid or a sterilization fluid without said cleaning liquid or sterilization fluid being able to enter the handle which is connected on the proximal side to the shaft. In this manner, an at least partial cleaning and/or sterilization of the interior of the shaft can be made possible, wherein at the same time the components of the handle, for example electric or electronic components which may be damaged by a cleaning liquid or a sterilization fluid, can be protected from the cleaning or sterilization fluid. Furthermore, by this means, when an endoscopic procedure is carried out with the medical instrument, contamination of the handle with body fluids, irrigation liquid and/or insufflation gas can be prevented.

The outer tube and/or the shaft housing preferably have/has an irrigation opening through which a cleaning liquid or a sterilization fluid can be introduced into the outer tube or into the shaft housing or can escape therefrom. In this case, in order to protect the handle from damage or soiling, the first seal is arranged on the proximal side of the irrigation opening. The second seal is preferably likewise arranged on the proximal side of the irrigation opening. The first and preferably also the second seal can at least be brought by displacement of the first or the second hollow tube into a respective position in which the first seal or the first and the second seal is/are arranged on the proximal side of the irrigation opening. By this means, it is possible, for example, on the proximal side to introduce a cleaning liquid or a sterilization fluid into the shaft, which cleaning liquid or sterilization fluid can escape from the shaft on the distal side. The cleaning or sterilization of the instrument according to the invention is thereby facilitated.

In a preferred manner, the first and the second seal are designed in such a manner that a sealing effect can be achieved over an entire displacement distance of the first and the second half tube or of the first and the second hollow tube. For this purpose, the first and the second seal can each be designed to slide on a cylindrical mating surface and, when the first hollow tube is displaced in relation to the second hollow tube and the first hollow tube is displaced in relation to the shaft housing, slide on a respective mating surface. By this means, sealing which is effective in any displacement position of the first and the second half tube and therefore a sealing effect which is independent of an operation or a position of the first functional element are made possible.

According to a preferred embodiment of the invention, the first and the second seal are connected to the first hollow tube. In particular, the first seal is fastened on an outer surface, and the second seal is fastened on an inner surface, of the first hollow tube. For this purpose, for example, the first seal, which is of substantially annular design, can be inserted into an encircling groove or into an annular recess of the outer surface of the first hollow tube and the likewise substantially annular second seal can be inserted into an encircling groove or recess of the inner surface of the first hollow tube. In this case, the inner surface of the shaft housing can be of substantially cylindrical design and can serve as a mating surface on which the first seal slides in a sealing manner when the first hollow tube is displaced in relation to the shaft housing. Furthermore, in this case, the outer surface of the second hollow tube can be of substantially cylindrical design in sections and can serve as a mating surface on which the second seal slides in a sealing manner when the second hollow tube is displaced in relation to the first hollow tube. This permits a particularly simple embodiment with reliable sealing.

Furthermore, it is preferred for the first and the second hollow tube to extend on the proximal side out of the shaft housing into the handle. For this purpose, the first and the second hollow tube can protrude on the proximal side out of the shaft housing such that they extend into the handle, wherein the handle can be attached on the proximal side to the shaft housing. It can also be provided that the shaft housing is connected to the handle via a connecting tube, wherein the first and the second hollow tube project beyond a proximal end of the connecting tube such that the first and the second hollow tube extend into the handle. It is thereby made possible in a simple manner that an operating device which is assigned to the first transmission element and is arranged within or on the handle acts on the first and the second hollow tube and, as a result, the first functional element of the tool arrangement can be operated by means of the operating device via the first transmission element formed by the first and the second hollow tube and the first and the second half tube.

Furthermore, it is preferred for the second transmission element to extend through the shaft housing and to extend on the proximal side into the handle. For this purpose, the second transmission element is designed in particular in such a manner that it projects on the proximal side beyond the shaft housing or, if a connecting tube is provided between the shaft housing and the handle, it projects beyond the proximal end of the connecting tube. It is thereby made possible that an operating device which is assigned to the second transmission element and is arranged in or on the handle acts on the second transmission element such that the second functional element of the tool arrangement can be operated by means of the operating device via the second transmission element.

In an advantageous manner, a further irrigation opening can be provided in the first transmission element, in particular in the first hollow tube. The further irrigation opening can be brought into overlap with the irrigation opening of the outer tube or of the shaft housing by displacement of the first hollow tube in the longitudinal direction of the shaft. This permits a cleaning liquid or a sterilization fluid to be introduced into an intermediate space between the first and the second hollow tube. Alternatively, a gap between the first and the second half tube can be usable for introducing irrigation fluid into the interior space of the first transmission element. By this means, the medical instrument is further improved in respect of the possibility for cleaning and/or sterilization.

According to a preferred embodiment of the invention, a likewise substantially annular third seal is arranged between an inner surface of the second hollow tube and an outer surface of the second transmission element. If an irrigation opening is provided in the first transmission element, the third seal is arranged on the proximal side of said irrigation opening. It is thereby made possible to introduce a cleaning liquid or a sterilization fluid into an intermediate space between the first and the second transmission element without said cleaning liquid or sterilization fluid being able to enter the handle; similarly, a penetration of body fluids or of irrigation or insufflation fluid into the handle can be more reliably avoided.

According to a preferred embodiment of the invention, the second transmission element is designed as a tension rod. The tension rod is displaceable in the longitudinal direction of the shaft relative to the outer tube and relative to the first transmission element. In particular, the tension rod can be displaceable with a corresponding operating device of the handle. The tension rod can transmit tensile forces and, at least to a limited extent, also shearing forces. This embodiment of the invention is of particularly simple and robust design and permits the transmission of high forces for operating the second functional element.

According to a further preferred embodiment of the invention, the second transmission element is designed as a substantially hollow-cylindrical inner tube, wherein an elongate third transmission element extends within the inner tube. The inner tube can be displaceable relative to the outer tube and/or can be rotatable about its longitudinal axis in order to operate the second functional element. For this purpose, a corresponding operating device of the handle can be assigned to the inner tube. The third transmission element can comprise, for example, one or more electric lines for transmitting a high-frequency voltage from the handle to the tool arrangement; for this purpose, a high-frequency voltage source can be connectable to the handle. As a result of the fact that the second transmission element is designed as an inner tube within which a third transmission element is arranged, further operating possibilities of the tool arrangement can be realized, and therefore the application possibilities of the medical instrument can be extended.

The first functional element of the tool arrangement is preferably designed as a bending portion which can be angled counter to a longitudinal axis of the shaft, wherein a proximal end of the bending portion is arranged at a distal end of the shaft, and the second functional element of the tool arrangement is arranged at a distal end of the bending portion. The bending portion can be angled in relation to the longitudinal axis of the shaft by displacement of the first half tube in relation to the second half tube and therefore by displacement of the first hollow tube relative to the second hollow tube. It is thereby made possible for the bending portion to be able to be activated by an operating device of the handle, which operating device is connected to the first transmission element. The bending portion has in particular an approximately identical outer diameter as a distal portion of the outer tube of the shaft, and therefore the bending portion, in a non-angled position, forms a rectilinear continuation of the shaft in the distal direction. In the case of an endoscopic procedure, this facilitates the introduction of the medical instrument according to the invention into a cavity, for example by means of an endoscopic introduction device.

According to a preferred embodiment of the invention, the second functional element is designed as a working tool which comprises at least one movable tool element which is operable via the second transmission element by means of an operating device of the handle, which operating device is assigned to the second transmission element. The working tool can comprise in particular two tool elements which are pivotable relative to each other, and therefore said tool elements can interact to open and close the working tool. The two tool elements can be pivotable here relative to a base of the second functional element, which base is arranged in particular at the distal end of the first functional element, or one tool element can be arranged in a stationary manner on the base and only the other designed to be pivotable. The tool elements can be designed, for example, as segments of scissors or as mouth parts of a grasping forceps. In particular, it can be provided that the at least one movable tool element can be moved by means of the operating device, which can act on the proximal side on the second transmission element, for example scissors or forceps can be opened or closed. The at least one movable tool element is preferably operable by displacement of the second transmission element. This provides a working tool which is simple to operate and is usable for a multiplicity of manipulations. The working tool is preferably designed in such a manner that it is arranged within a distal-side extension of the outer surface of the outer tube in a starting position of the at least one movable tool element and in an extended position of the bending portion; by this means, the introduction of the medical instrument according to the invention into a cavity inside a body is facilitated.

Furthermore, it is preferred for the working tool to be rotatable about a longitudinal axis of the working tool. The second transmission element is preferably designed as an inner tube, wherein a rotation of the inner tube about the longitudinal axis of the shaft brings about a corresponding rotation of the working tool, in particular a base of the working tool that is arranged at the distal end of the bending portion, about its longitudinal axis. For this purpose, the inner tube can be guided through the bending portion of the tool arrangement and can be of correspondingly flexible design. This permits particularly versatile usability of the working tool.

According to a further embodiment of the invention, the medical instrument has the features of the precharacterizing clause of Claim 1 and, as described above, a shaft housing which is enlarged in relation to the shaft and is connected to the outer tube in a proximal end portion of the shaft. In this embodiment, the first half tube and the second half tube of the first transmission element extend through the shaft housing, wherein a seal is arranged between an inner surface of the shaft housing and the outer surfaces of the first and of the second half tube, which seal is preferably of substantially annular design and which is referred to below as the outer seal. The outer seal lies in a sealing manner against a preferably cylindrical inner surface of the shaft housing and likewise in a sealing manner against the outer surface of the first transmission element which is formed by the first and the second half tube. The outer seal can be fixedly connected in particular to an inner surface of the shaft housing and can be inserted, for example, into an encircling groove in the inner surface of the shaft housing. Otherwise, the medical instrument according to this embodiment can be designed as described previously. Owing to the fact that a seal is arranged between the inner surface of the shaft housing and the outer surface of the first transmission element, an entry of cleaning liquid or sterilization fluid into the handle can also be prevented in this embodiment of the invention.

The first half tube and the second half tube preferably face each other with their open longitudinal sides and in each case form a gap between their longitudinal sectional surfaces; the effect which can thereby be achieved is that the first half tube is displaceable in relation to the second half tube with particularly little friction. Furthermore preferably, a further seal which is likewise substantially annular and is referred to below as the inner seal is arranged between an inner surface of the first transmission element, i.e. between the inner surfaces of the first and the second half tube, and the outer surface of the second transmission element. In this case, the outer seal arranged between the shaft housing and the first and the second half tube has two webs which protrude inward opposite each other, extend in the longitudinal direction of the shaft and each project into one of the gaps and lie in a sealing manner against the longitudinal sectional surfaces of the half tubes and against the inner seal. The sealing can thereby be further improved.

It goes without saying that the features mentioned above and those which have yet to be explained below are usable not only in the respectively stated combination, but also in other combinations or on their own without departing from the scope of the present invention.

BRIEF DESCRIPTION OF THE DRAWINGS

Further aspects of the invention emerge from the description below of two preferred exemplary embodiments and the attached drawing, in which:

FIGS. 4A and 4B show a portion of the shaft of a medical instrument according to a second exemplary embodiment of the invention in an oblique view and in an enlargement of a detail;

DETAILED DESCRIPTION

Figure 1A:
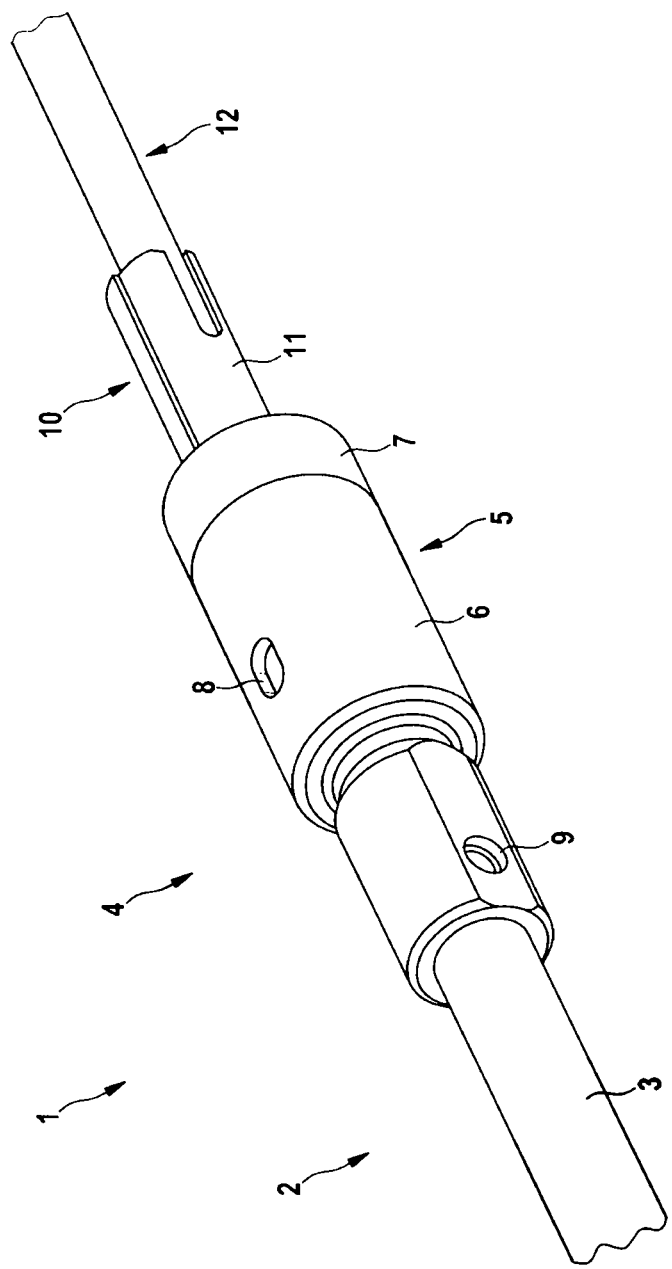
FIGS. 1A and 1B show a portion of the shaft of a medical instrument according to a first exemplary embodiment of the invention in an oblique view and in a view sectioned in the longitudinal direction, in each case in a first relative position of the first and the second half tube.
Figure 1B:
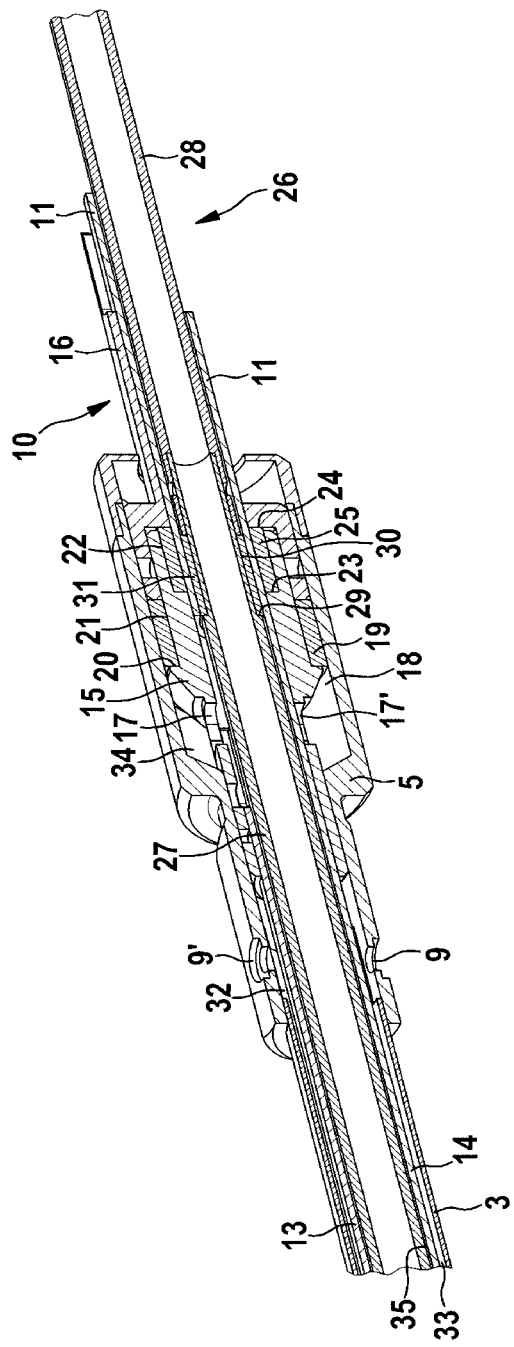
Figure 2A:
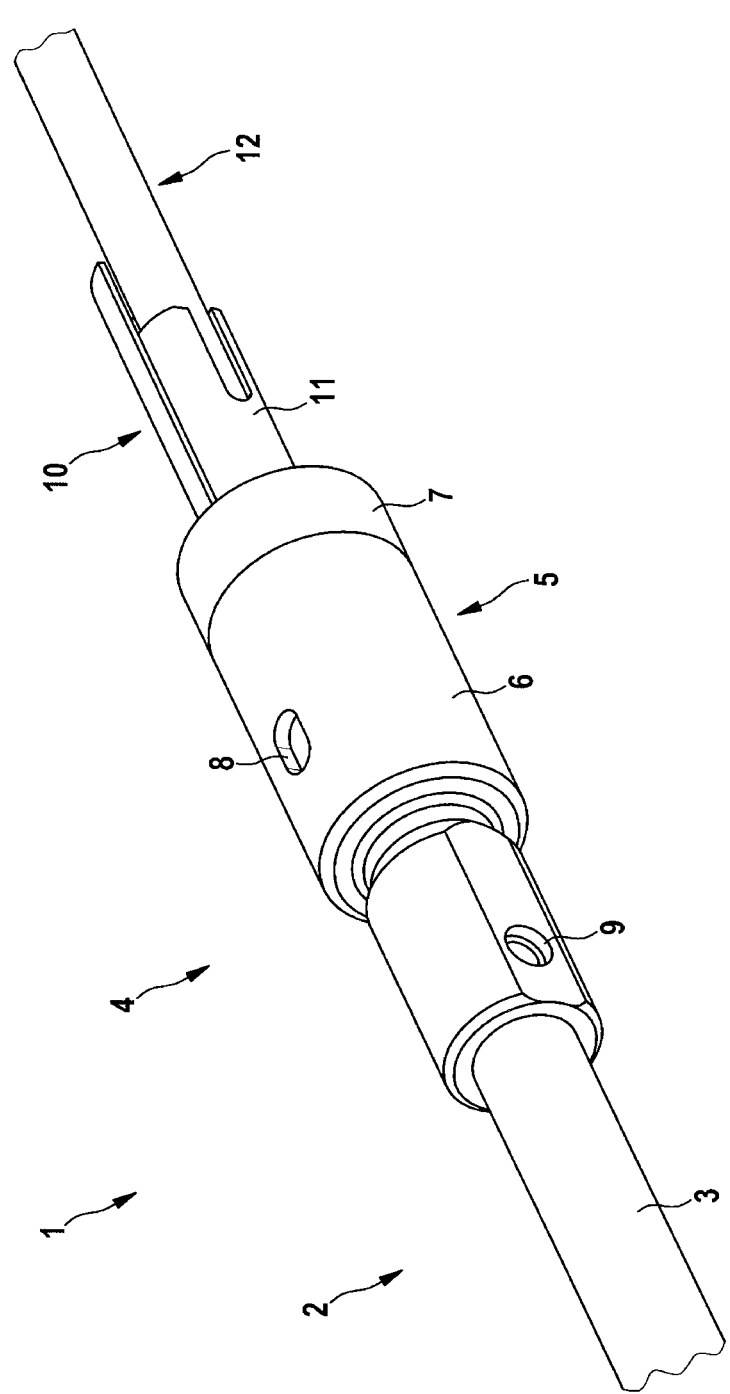
FIGS. 2A and 2B show the portion of the shaft according to FIGS. 1a and 1b, but in a second relative position of the first and the second half tube.
Figure 2B:
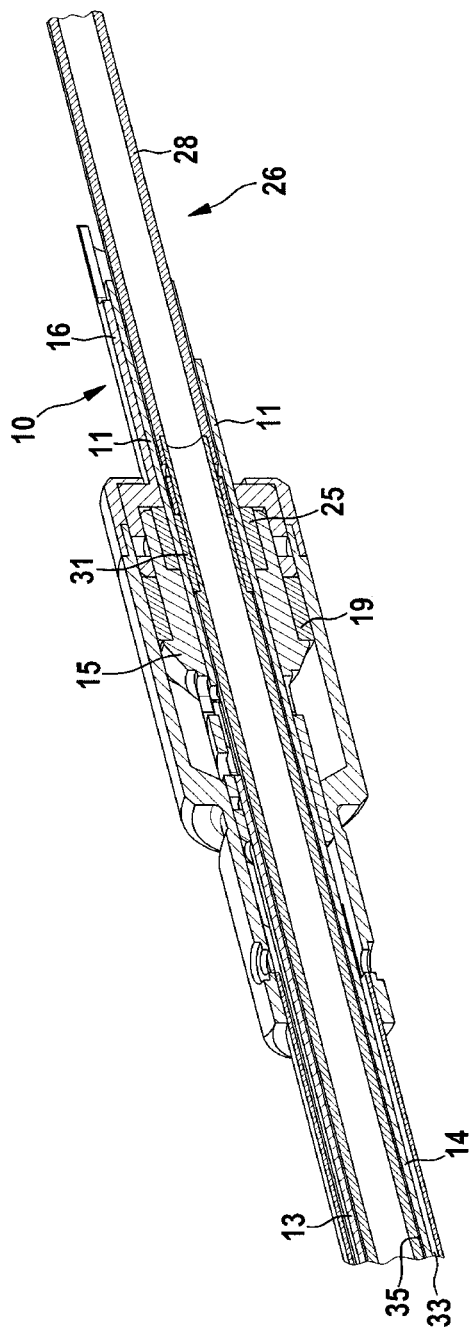

FIGS. 1a and 1b illustrate a portion of the shaft 1 of a medical instrument according to a first exemplary embodiment of the invention in an oblique view and in a sectional view. The illustrated medical instrument is designed as an endoscopic instrument. As shown in FIG. 1a, the shaft 1 comprises a distal portion 2 with a hollow-cylindrical outer tube 3, wherein the distal portion 2 is intended for introduction into a cavity inside a human or animal body, and a proximal end portion 4 with a shaft housing 5 which is enlarged in relation to the outer tube 3 and, in the case of an endoscopic procedure, remains outside the body. The shaft housing 5 comprises a main body 6 and an end cap 7 attached to the latter on the proximal side, and optionally further components (not shown in FIGS. 1a and 1b), such as, for example, an irrigation connection stub. The main body 6 has a first irrigation opening 8 and a second irrigation opening 9 through which a cleaning liquid can be introduced or discharged. In the exemplary embodiment illustrated, the shaft housing 5 is of substantially cylindrical design in sections on the outer side, but with a larger outer diameter than the outer tube 3. As indicated in FIG. 1a, proximal portions of a first hollow tube 10, a second hollow tube 11 and an inner tube 12 extending within the second hollow tube 11 protrude on the proximal side out of the shaft housing 5 and into a handle (not illustrated in FIGS. 1a and 1b) which adjoins the shaft housing 5 on the proximal side. As likewise not illustrated in FIGS. 1a and 1b, a tool arrangement with which surgical manipulations can be carried out in a cavity inside a body is arranged at a distal end of the distal portion 2 of the shaft 1.

In FIG. 1b, the proximal end portion 4 is shown in a longitudinal section. The sectional plane is a plane which is horizontal in the illustration of FIG. 1a and in which the center longitudinal axis of the shaft 1, which corresponds to the center longitudinal axis of the outer tube 3, extends. In the sectional view shown in FIG. 1b, the irrigation opening 9 provided in the distal part of the shaft housing 5 and the irrigation opening 9' lying opposite said irrigation opening 9 are cut away. The irrigation opening 8 cannot be seen in FIG. 1b. The outer tube 3 is inserted in a sealed manner into the distal part of the main body 5 and is fixedly connected thereto, for example by adhesive bonding, soldering or welding. That portion of the outer tube 3 which is inserted into the main body 5 is cut off in order not to conceal the irrigation openings 9, 9'. A first half tube 13 and a second half tube 14 which each have a semicircular cross section and are attached to each other with their open sides are arranged within the outer tube 3. The half tubes 13, 14, which are each sectioned approximately in a center longitudinal plane in the longitudinal section illustrated in FIG. 1b, therefore together form a substantially hollow-cylindrical tube arrangement. The first half tube 13 and the second half tube 14 are each mounted displaceably in the outer tube 3, in the longitudinal direction thereof. The first half tube 13 is fixedly connected in its proximal end portion to the first hollow tube 10, for example by adhesive bonding, soldering or welding. The first hollow tube 10 consists of a distal tube portion 15 and a proximal tube portion 16, wherein the distal tube portion 15 is connected on the distal side to the first half tube 13 and on the proximal side to the proximal tube portion 16. The first hollow tube 10 is displaceable together with the first half tube 13 in the longitudinal direction of the shaft 1. The distal tube portion 15 has irrigation openings 17, 17' and optionally further openings and is otherwise designed as a circumferentially closed tube, i.e. as a tube which extends over 360°, as seen from its center longitudinal axis. The distal tube portion 16 is likewise designed in sections as a circumferentially closed tube and as a half tube in a proximal end portion. The second half tube 14 is connected integrally to the second hollow tube 11, wherein the second hollow tube 11 is closed circumferentially in sections.

The main body 6 of the shaft housing 5 has a cylindrical inner surface 18 in its proximal part. A first seal 19 which is of annular design and is inserted on the outer side of the first hollow tube 10 into an annular recess 21 formed between a step 20 and the distal end of the proximal tube portion 16 lies in a sealing manner against the inner surface 18. A second seal 25 which is likewise of annular design and lies in a sealing manner on a cylindrical outer surface of a circumferentially closed portion of the second hollow tube 11 is inserted on the inner side of the first hollow tube 10 into an annular recess 22 which is formed between a step 23 of the distal tube portion 15 and a step 24 of the proximal tube portion 16. The seals 19, 25 are designed, for example, as short cylindrical flexible tube portions.

An inner tube 26 which is assembled from a distal tube portion 27 and a proximal tube portion 28, which are fixedly connected to each other, is arranged within the tube arrangement formed by the first half tube 13 and the second half tube 14 and within the second hollow tube 11. The inner tube 26 has an inner surface which is of substantially cylindrical design and in which further transmission elements (not illustrated in the figures) can extend. An annular recess 30 into which a third seal 31 is inserted which is likewise of annular design, for example as a short cylindrical flexible tube portion, is formed between a step 29 of the distal tube portion 27 and the distal end of the proximal tube portion 28. The third seal 31 lies in a sealing manner against a cylindrical inner surface of the second hollow tube 11. The proximal tube portion 16 of the first hollow tube 10, the second hollow tube 11 and the inner tube 26 protrude on the proximal side beyond the shaft housing 5 and into a handle (not illustrated), which adjoins the shaft housing 5 on the proximal side, where they are connected to corresponding operating devices.

The irrigation openings 9, 9' are connected to a first cavity 32 within the shaft housing 4, which cavity is fluidically connected to an intermediate space 33 between the outer tube and the first half tube 13 or the second half tube 14. The irrigation opening 8 (not visible in FIG. 1b) opens into a second cavity 4 of the shaft housing 4, which cavity is connected via the irrigation openings 17, 17' to an intermediate space 35 between the first half tube 13 or the second half tube 14 and the inner tube 26. A cleaning liquid or a sterilization fluid can be introduced into the shaft 1 through the irrigation openings 8, 17, 17' and conducted in the distal direction through the intermediate space 35 between the half tubes 13, 14 and the inner tube 26 and can escape there, as well as through the irrigation openings 9, 9' and through the intermediate space 33 between the outer tube and the half tubes 13, 14. The intermediate spaces 33, 35 also permit sufficient play such that a low-friction displacement of the half tubes 13, 14 and of the inner tube 26 in the axial direction is possible.

The described conducting through of cleaning liquid permits cleaning of the components arranged in the outer shaft 3 and also optionally of further components of the tool arrangement (not illustrated in the figures); similarly, sterilization can be made possible by conducting through a sterilization fluid. At the same time, the seals 19, 25, 31 prevent the cleaning liquid or the sterilization fluid from escaping in the proximal direction and therefore penetrating into the handle which is attached on the proximal side to the shaft housing 4 and into which the first hollow tube 10, the second hollow tube 11 and the inner tube 26 project. The seals 19, 25, 31 can consist of PTFE (Teflon) or of another suitable sealing material.

In order to operate a first functional element of the tool arrangement arranged at the distal end of the distal portion 2 of the shaft 1, for example in order to angle a bending portion of the tool arrangement in relation to the longitudinal axis of the shaft 2 of the medical instrument, the first half tube 13 and the second half tube 14 are mutually displaced. For this purpose, an operating device is provided within the handle, the operating device being connected to the first hollow tube 10 and to the second hollow tube 11 and bringing about an oppositely directed, equally sized displacement of the first hollow tube 10 and of the second hollow tube 11 in relation to the handle and to the shaft housing 5 connected to the latter. Said operating device may comprise, for example, a gear wheel which is operable in a motorized manner and is arranged between a rack connected to the first hollow tube 10 and a rack connected to the second hollow tube 11 and engages in said racks. The oppositely directed displacement of the first hollow tube 10 and of the second hollow tube 11 brings about a displacement of the first half tube 13 in relation to the second half tube 14 and a corresponding actuation of the first functional element, for example an angling of a bending portion of the tool arrangement via sliding elements.

Figure 3A:
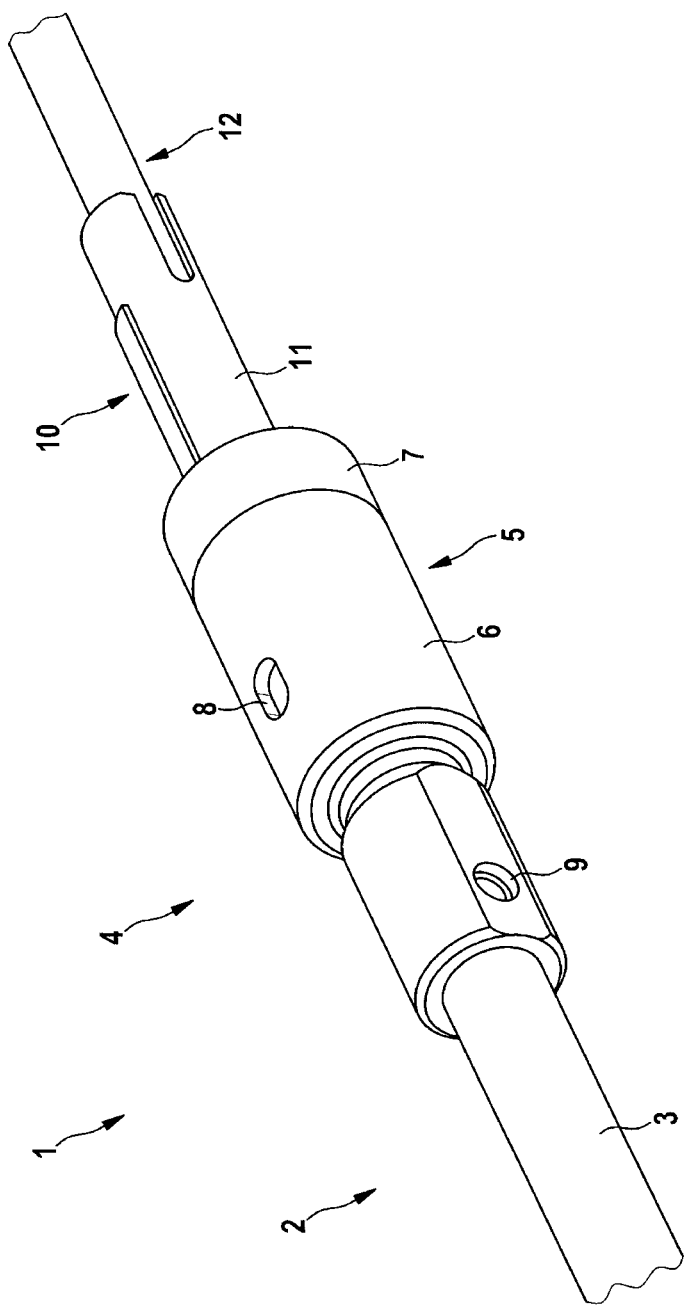
FIGS. 3A and 3B show the portion of the shaft according to FIGS. 1a and 1b, but in a third relative position of the first and the second half tube.
Figure 3B:
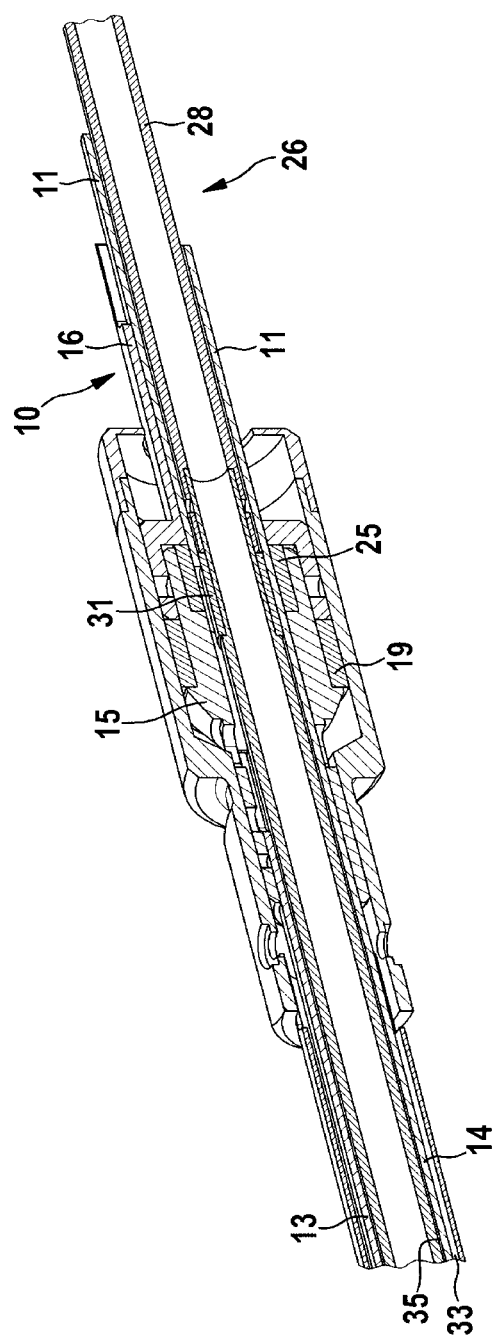

The two extreme positions of the relative movement of the first hollow tube 10 relative to the second hollow tube 11 or of the first half tube 13 relative to the second half tube 14 are illustrated in FIGS. 2a to 3b, in illustrations which each correspond to the views shown in FIGS. 1a and 1b, whereas FIGS. 1a and 1b each show a central position. In the position shown in FIGS. 2a and 2b, the first hollow tube 10 is displaced in the proximal direction in relation to the position shown in FIGS. 1a and 1b, and the second hollow tube 11 is displaced in the distal direction. Accordingly, the first seal 19 lies against a region of the inner surface 18 of the main body 5 of the shaft housing 4, which region is displaced in the proximal direction; the second seal 25 and, if the position of the inner tube 26 is unchanged, the third seal 31 are displaced on the outer or the inner surface of the second hollow tube 11 in the proximal direction in relation to the position shown in FIGS. 1a and 1b. Secondly, a maximum displacement of the first hollow tube 10 in relation to the second hollow tube 11 in the distal direction is illustrated in FIGS. 3a and 3b. In this case, the first seal 19 lies against a region of the inner surface 18 of the main body 5, which region is displaced in the distal direction, and the second seal 25 and the third seal 31 are displaced on the outer or the inner surface of the second hollow tube 11 in the distal direction. As can be seen in FIGS. 1b and 2b, the above-described fluid connection between the irrigation opening 8 and the intermediate space 35 and between the irrigation openings 9, 9' and the intermediate space 33 also exists in the two end positions. The introduction of a cleaning liquid or of a sterilization fluid is therefore independent of the operating position of the first and also of the second functional element.

FIG. 4a shows a portion of the shaft 1 of a medical instrument according to a second exemplary embodiment of the invention in a view corresponding to FIG. 1a, wherein the shaft housing 5 is illustrated transparently. FIG. 4b shows an enlargement of a detail. As shown in FIG. 4a, a first half tube 36 and a second half tube 37 and also the inner tube 26 extend through the shaft housing and protrude on the proximal side from the latter such that they extend into a handle (not illustrated) attached to the shaft housing 5, where corresponding operating devices are provided. A substantially annular seal 38 which provides a seal outside the half tubes 36, 37 and is also referred to here as the outer seal 38 is arranged between the cylindrical inner surface 18 of the shaft housing 5 and the half tubes 36, 37. The outer seal 38 is shaped cylindrically on the outer side and lies in a sealing manner against the inner surface 18 of the shaft housing 5. On its inner side, the outer seal 38 lies in a sealing manner against the outer sides of the half tubes 36, 37 and reaches with an inwardly protruding projection, which is designed as a web 39 running in the axial direction (see FIGS. 5a, 5b), into a gap 41 formed between the longitudinal sectional surfaces 40, 40' of the half tubes 36, 37. On that side of the outer seal 38 which is opposite the web 39, an axial web 39' likewise protrudes inward and engages in a corresponding gap between the other longitudinal sectional surfaces (not visible in FIGS. 4a and 4b) of the half tubes 36, 37. In an annular recess, the inner tube 26 bears a further seal 42 which provides a seal in the half tubes 36, 37 and which is therefore referred to here as the inner seal. The inner seal 42 is substantially designed in the manner of the third seal 31 described in the first exemplary embodiment, but provides a seal between the inner tube 26 and the half tubes 36, 37 and the webs 39, 39' of the outer seal 38. The outer seal 38 can be fastened, for example, to the inner surface 18 of the shaft housing 5 and can slide in a sealing manner on the half tubes 36, 37 and on the inner seal 42 when the half tubes 36, 37 and the inner tube 26 are displaced axially.

Figure 5B:
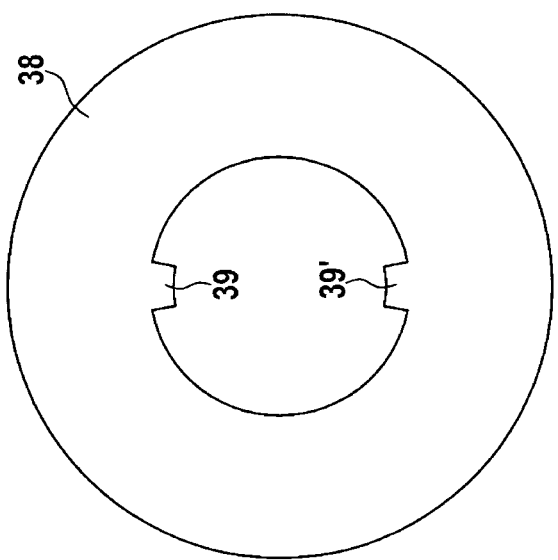
FIGS. 5A and 5B show an outer seal according to the second exemplary embodiment of the invention in an oblique view and in an end-side view.
Figure 5A:
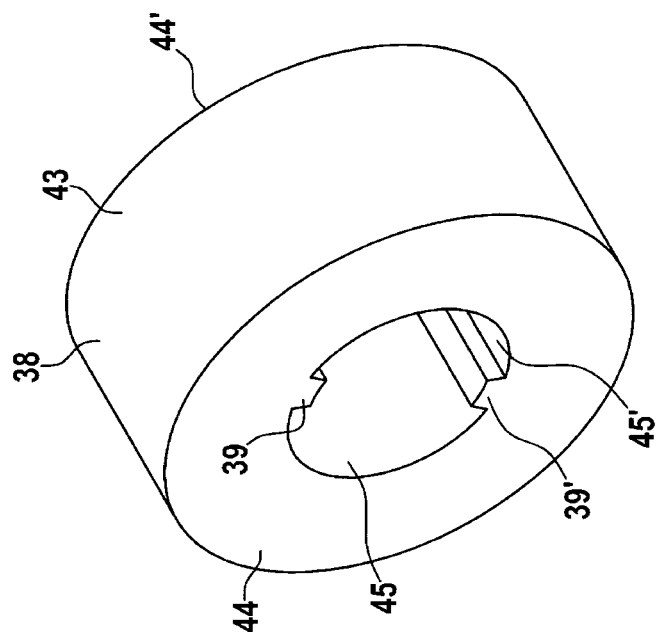

FIGS. 5a and 5b illustrate the outer seal 38 in more detail. The outer seal 38 has a cylindrical outer surface 43 and substantially flat end surfaces 44, 44' in the axial direction. The inner surface of the outer seal 38 has two approximately semi-cylindrical regions 45, 45' which are separated from each other by the two inwardly projecting webs 39, 39' running in the axial direction. The outer seal 38 can be composed, for example, of silicone or of another suitable sealing material.

Otherwise, the medical instrument according to the first and the second exemplary embodiment of the invention can be designed as described in European patent application EP 2 837 354 A1 which is incorporated in this regard by reference into the present application. In particular, the tool arrangement which is arranged at the distal end of the shaft 2 and which is not illustrated in FIGS. 1a to 5b can be designed as described in EP 2 837 354 A1 and can comprise a bending portion and a gripper. The handle which is not illustrated in FIGS. 1a to 5b can also be designed in accordance with EP 2 837 354 A1.

Figure 6:
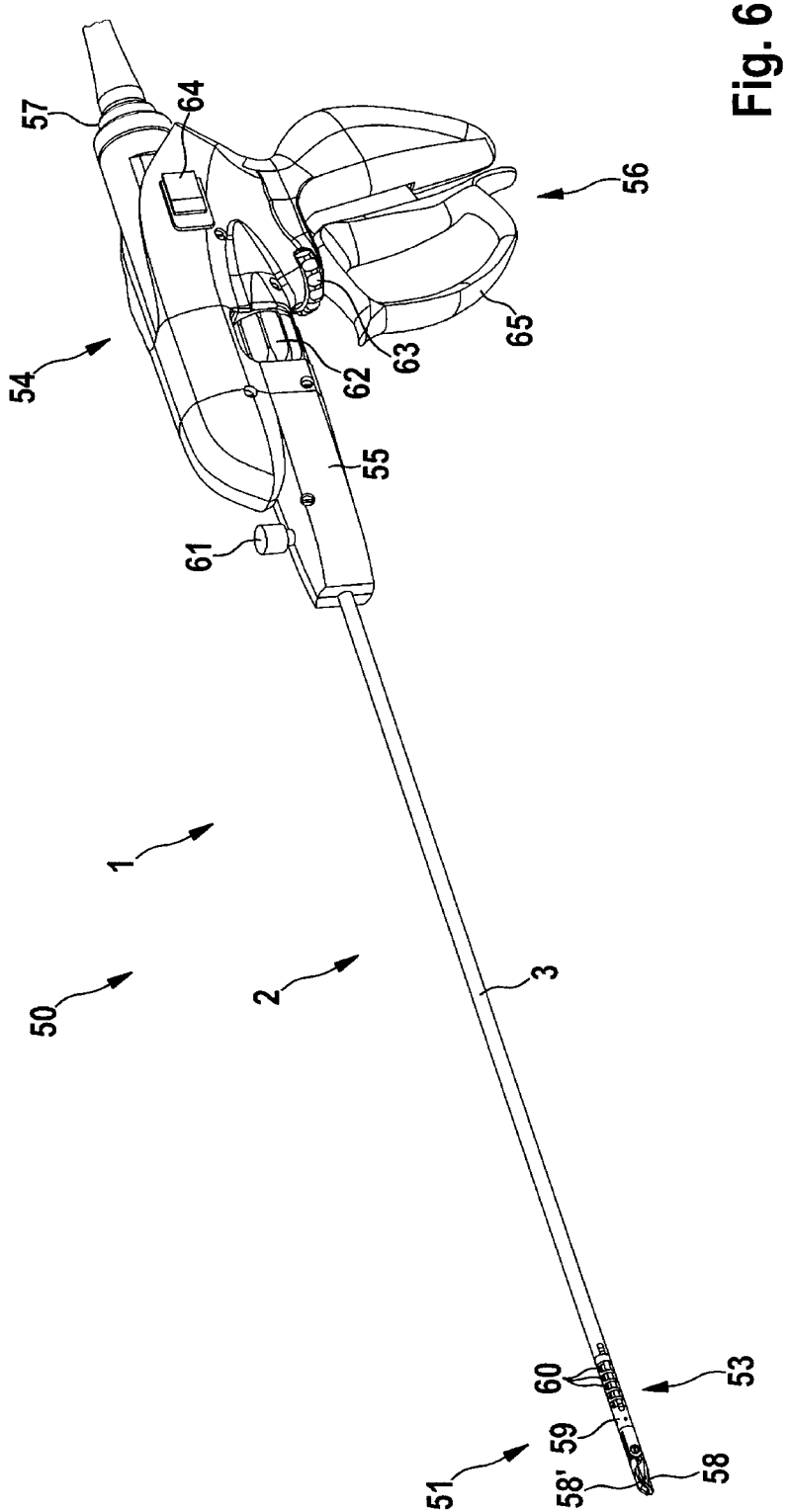
FIG. 6 shows a medical instrument according to the first and the second exemplary embodiment of the invention in an overall view.

A medical instrument, the shaft of which is designed as described previously according to the first and the second exemplary embodiment, can be configured overall as shown in FIG. 6. The medical instrument 50 which is designed as an endoscopic instrument has a shaft 1 with a distal portion 2, a tool arrangement 51 with a working tool designed as forceps 52 and a bending portion 53, and also a handle 54 with a housing 55, a hand grip 56 and a connection 57. A proximal end portion of the shaft 1 is accommodated in the housing 55. The distal portion 2 and the proximal end portion are designed in accordance with the previously described first or second exemplary embodiment.

The forceps have two mouth parts 58, 58' which are coupled pivotably to a base 59. The base 59 is rotatable about its longitudinal axis which, in the extended position of the bending portion 53 that is shown in FIG. 6, coincides with the longitudinal axis of the distal portion 2 of the shaft 1. The bending portion 53 comprises a plurality of hinge elements 60 which are connected to one another via hinges and can be pivoted in relation to one another by means of sliding elements.

The housing 55 of the handle 54 bears an irrigation connection stub 61 to which a flexible feed or discharge tube for a cleaning liquid can be connected and which is connected to the irrigation opening 8 or 9 or 9' (see FIGS. 1a to 4b). Control elements 62, 63, 64 for the manual or motorized control of the bending of the bending portion 53, of the rotation of the base 59 of the forceps 52 about its longitudinal axis and for controlling a charging of the forceps 52 with monopolar or bipolar high-frequency voltage are arranged on the housing 55. A contact connection for transmitting the high-frequency voltage to the forceps 52, which are rotatable about the longitudinal axis of the base 59, can take place here via sliding contacts, in particular in the case in which the medical instrument is designed as bipolar forceps. By movement of the gripping ring 65 of the hand grip 56, the forceps 52 can be opened and closed.

A first transmission element for operating the bending portion 53, a second transmission element for operating the forceps 52 and a third transmission element for transmitting the high-frequency voltage to the mouth parts 58, 58' extend within the distal portion 2 of the shaft 1. The first and the second transmission element extend into the handle 54 where they are connected to operating devices which can be controlled by the corresponding control elements 62, 63 and the gripping ring 65. The third transmission element is connected to the connection 57, to which a high-frequency voltage source can be connected, and can be interrupted by the further control element 64. The transmission elements mentioned and the shaft 1 are designed as described previously in accordance with the first or the second exemplary embodiment of the invention. Otherwise, the medical instrument 50 can be designed as described in European patent application EP 2 837 354 A1 which is also incorporated with respect to the previously described exemplary embodiment of the medical instrument that is shown in FIG. 6 by reference into the present application.

For the sake of clarity, all reference signs are not illustrated in all of the figures. Reference signs not explained in a figure have the same meaning as in the other figures.

What is claimed is:
1. A medical instrument, comprising:
an elongate shaft;

a tool arrangement arranged at a distal end of the shaft; and a handle, which is arranged at a proximal end of the shaft, for operating the tool arrangement;

wherein the shaft has an elongate outer tube, within which there is arranged a first transmission element for transmitting an operating movement from the handle to the tool arrangement in order to operate at least one first functional element of the tool arrangement;

wherein the first transmission element comprises a first half tube and a second half tube, wherein the first half tube and a second half tube are mutually displaceable in a longitudinal direction of the shaft in order to operate the at least one first functional element;

wherein a second transmission element for transmitting an operating movement from the handle to the tool arrangement in order to operate at least one second functional element of the tool arrangement is arranged in an elongate cavity formed by the first half tube and the second half tube;

wherein a shaft housing is enlarged in relation to the shaft and is connected to the outer tube is arranged in a proximal end portion of the shaft;

wherein a first hollow tube which is connected to the first half tube is arranged within the shaft housing, and a second hollow tube which is connected to the second half tube is arranged within the first hollow tube; and wherein a substantially annular first seal is arranged between an inner surface of the shaft housing and an outer surface of the first hollow tube, and a substantially annular second seal is arranged between an inner surface of the first hollow tube and an outer surface of the second hollow tube.

2. The medical instrument according to claim 1, wherein the outer tube and/or the shaft housing have/has an irrigation opening, and the first seal is arranged on a proximal side of the irrigation opening.

3. The medical instrument according to claim 1, wherein when the first hollow tube and the second hollow tube are displaced in the longitudinal direction of the shaft, the first seal slides in a sealing manner on the inner surface of the shaft housing and/or on the outer surface of the first hollow tube, and the second seal slides in a sealing manner on the inner surface of the first hollow tube and/or on the outer surface of the second hollow tube.

4. The medical instrument according claim 1, wherein the first and the second seal are connected to the first hollow tube.

5. The medical instrument according to claim 1, wherein the first hollow tube and the second hollow tube extend out of the shaft housing into the handle.

6. The medical instrument according to claim 1, wherein the second transmission element extends out of the shaft housing into the handle.

7. The medical instrument according to claim 1, wherein the first transmission element has at least one irrigation opening.

8. The medical instrument according to claim 1, wherein a substantially annular third seal is arranged between an inner surface of the second hollow tube and an outer surface of the second transmission element.

9. The medical instrument according to claim 1, wherein the second transmission element is a tension rod.

10. The medical instrument according to claim 1, wherein the second transmission element is an inner tube, wherein an elongate third transmission element is arranged within the inner tube.

11. The medical instrument according to claim 1, wherein the first functional element of the tool arrangement is a bending portion which can be angled in relation to a longitudinal axis of the shaft, wherein the second functional element is arranged at a distal end of the bending portion.

12. The medical instrument according to claim 1, wherein the second functional element is a working tool with at least one movable tool element which is operable by displacement of the second transmission element in the longitudinal direction of the shaft.

13. The medical instrument according claim 1, wherein the working tool is rotatable about a longitudinal axis of the working tool by rotation of the second transmission element about the longitudinal axis of the shaft.

14. The medical instrument according to claim 1, wherein the first half tube and the second half tube extend through the shaft housing, wherein a seal is arranged between an inner surface of the shaft housing and the outer surfaces of the first half tube and of the second half tube.

15. The medical instrument according to claim 14, wherein an open longitudinal side of the first half tube and an open longitudinal side of the second half tube face each other, wherein a gap is formed between a longitudinal sectional surface of the first half tube and a longitudinal sectional surface of the second half tube, and a substantially annular inner seal is arranged between an inner surface of the first half tube, an inner surface of the second half tube, and an outer surface of the second transmission element, and the seal arranged between the inner surface of the shaft housing and the respective outer surfaces of the first half tube and of the second half tube has two axially extending webs which protrude inwards opposite each other, and in each case project into the gap and lie in a sealing manner against the respective longitudinal sectional surfaces of the first half tube and of the second half tube and against the inner seal.

16. The medical instrument according to claim 2, wherein when the first hollow tube and the second hollow tube are displaced in the longitudinal direction of the shaft, the first seal slides in a sealing manner on the inner surface of the shaft housing and/or on the outer surface of the first hollow tube, and the second seal slides in a sealing manner on the inner surface of the first hollow tube and/or on the outer surface of the second hollow tube.

17. The medical instrument according claim 2, wherein the first and the second seal are connected to the first hollow tube.

18. The medical instrument according to claim 2, wherein the first hollow tube and the second hollow tube extend out of the shaft housing into the handle.

19. The medical instrument according to claim 2, wherein the second transmission element extends out of the shaft housing into the handle.

20. The medical instrument according to claim 2, wherein the first transmission element has at least one irrigation opening.

* * * * *